United States Patent
Zeyher et al.

(10) Patent No.: US 10,661,002 B2
(45) Date of Patent: May 26, 2020

(54) PERITONEAL DIALYSIS MACHINE

(71) Applicant: FRESENIUS MEDICAL CARE DEUTSCHLAND GMBH, Bad Homburg (DE)

(72) Inventors: Peter Zeyher, Darmstadt (DE); Kim Fritsch, Trebur (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 101 days.

(21) Appl. No.: 15/752,114

(22) PCT Filed: Aug. 10, 2016

(86) PCT No.: PCT/EP2016/001378
§ 371 (c)(1),
(2) Date: Feb. 12, 2018

(87) PCT Pub. No.: WO2017/025196
PCT Pub. Date: Feb. 16, 2017

(65) Prior Publication Data
US 2018/0236153 A1    Aug. 23, 2018

(30) Foreign Application Priority Data

Aug. 11, 2015    (DE) .................. 10 2015 010 468

(51) Int. Cl.
*A61M 1/28*    (2006.01)
*A61M 1/16*    (2006.01)
(Continued)

(52) U.S. Cl.
CPC ............ *A61M 1/1643* (2014.02); *A61M 1/28* (2013.01); *A61M 2205/3379* (2013.01);
(Continued)

(58) Field of Classification Search
CPC .................. A61M 1/28; A61M 1/1643; A61M 2205/3379; A61M 2205/3393; G01G 23/3735; G01G 19/56
(Continued)

(56) References Cited

U.S. PATENT DOCUMENTS 4,479,561 A    10/1984    Feinland et al.
4,726,435 A    2/1988    Kitagawa et al.
(Continued)

FOREIGN PATENT DOCUMENTS

| CN | 105444862 | * 3/2016 | ............. G01G 19/44 |
|---|---|---|---|
| DE | 60029744 | 8/2007 | |
| WO | WO 84/02277 | 6/1984 | |

*Primary Examiner* — Jacques M Saint Surin
(74) *Attorney, Agent, or Firm* — Jacobson Holman, PLLC.

(57) ABSTRACT

A peritoneal dialysis machine has a machine housing and a drain pan for receiving one or more solution bags for storing consumed dialysate. The drain pan is connected to a weighing cell such that the weight of the drain pan can be detected by the weighing cell. A damping system prevents the occurrence of undue force introduction into the weighing cell. The damping system has a damper to which the drain pan is directly or indirectly fastened, and the damper is connected to the weighing cell such that the weight of the drain pan acting thereon is transmitted to the weighing cell.

21 Claims, 3 Drawing Sheets

(51) Int. Cl.
*G01G 19/56* (2006.01)
*G01G 23/37* (2006.01)

(52) U.S. Cl.
CPC ..... *A61M 2205/3393* (2013.01); *G01G 19/56* (2013.01); *G01G 23/3735* (2013.01)

(58) Field of Classification Search
USPC .......................................................... 177/154
See application file for complete search history.

(56) References Cited

U.S. PATENT DOCUMENTS

| | | | |
|---|---|---|---|
| 5,116,312 A | 5/1992 | Blankenship et al. | |
| 6,907,409 B1* | 6/2005 | Huebler | G01G 19/005 |
| | | | 177/185 |
| 9,358,331 B2* | 6/2016 | Fulkerson | A61M 1/3641 |
| 9,433,720 B2* | 9/2016 | Updyke | A61M 1/284 |
| 9,861,733 B2* | 1/2018 | Burbank | A61M 1/285 |
| 9,907,897 B2* | 3/2018 | Burbank | A61M 1/1656 |
| 10,035,103 B2* | 7/2018 | Fulkerson | A61M 1/14 |
| 10,066,983 B2* | 9/2018 | Groeber | A61M 1/288 |
| 2009/0187138 A1 | 7/2009 | Lundtveit et al. | |
| 2011/0160649 A1 | 6/2011 | Pan | |
| 2018/0043076 A1* | 2/2018 | Gerber | A61M 1/1613 |
| 2018/0333527 A1* | 11/2018 | Wen | F04B 13/00 |

\* cited by examiner

PERITONEAL DIALYSIS MACHINE

BACKGROUND OF THE INVENTION

1. Field of the Invention

The present invention relates to a peritoneal dialysis machine having at least one machine housing and having at least one drain pan for receiving one or more solution bags for storing consumed dialyzate, wherein the drain pan is connected to at least one weighing cell such that the weight of the drain pan can be detected by means of the weighing cell.

2. Description of Related Art

With peritoneal dialysis machines known from the prior art, a pan, also called a drain pan in the following, is located beneath the machine housing and serves the receiving of one or more bags which are filled with dialyzate which is drained from the patient. This pan is connected via a connection mechanism such as a linkage, to a weighing cell which is typically located in or at the machine housing. The weighing cell determines the weight of the drain pan or of the bag or bags located therein.

On an undue action of force or on an uneven load distribution in the drain pan, a state can occur which overloads or damages the weighing cell. Such an undue load or action of force can occur, for example, if the user of the machine accidentally deflects the drain pan beyond a specific amount or, for example, also when the drain pan is loaded with solution bags outside the center of gravity. Vibrations of the drain pan can also result in damage to or an overload of the weighing cell.

SUMMARY OF THE INVENTION

It is therefore the underlying object of the present invention to further develop a peritoneal dialysis machine of the initially named kind such that an overload of the weighing cell is reliably prevented in a comparatively simple manner.

This object is achieved by a peritoneal dialysis machine of the initially named kind in that at least one damping system is provided which prevents the occurrence of undue force introduction into the weighing cell. The damping system has at least one damper to which the drain pan is directly or indirectly fastened, preferably via a holder, wherein the damper is connected to the weighing cell such that the weight of the drain pan acting thereon is transmitted to the weighing cell.

Provision is thus made in accordance with the invention that the drain pan or its holder, such as a linkage or the like, is not directly connected to the weighing cell, but is rather connected indirectly via at least one damper. This damper protects the weighing cell not only against undue action of force or against the consequences of uneven load distribution, but also damps vibrations into which the drain pan was accidentally set. The load on the weighing cell is thus-correspondingly reduced since the movements or the forces and torques which act on the drain pan are not transmitted to the weighing cell directly, but rather indirectly and in a damped form.

The damping system can thus act as a force and torque restricting device which damps or reduces the torque acting on the weighing cell or the force acting on the weighing cell—caused by the drain pan or its holder.

It is pointed out at this point that the term "weight of the drain pan" covers both the weight of the empty drain pan and the weight of the drain pan filled with one or more solution bags.

It is furthermore pointed out that the term "solution bag" is used as representative for any container with rigid or flexible walls which is suitable for receiving consumed dialyzate. The term is thus not restricted to a bag in the narrower sense.

Finally, it is pointed out that the term "drain pan" can include any desired receptacle, e.g. for one or more bags or containers having flexible or non-flexible walls and can also stand for any desired vessels into which a liquid, preferably consumed dialysis solution, can be received. The "drain pan" can thus, for example, also directly be a container or a bag that is connected to the weighing cell and whose weight is measured—irrespective of whether a pan for receiving the container or bag is used or not.

It is furthermore pointed out that the weighing cell is preferably arranged in a housing of the weighing cell or forms a component of the housing of the weighing cell.

In a preferred embodiment of the invention, the damping system is furthermore configured such that the drain pan or its holder does not come into connection with one or more further elements of the peritoneal dialysis machine, which would have the consequence of a falsification of the measurement result.

Provision is made in a preferred embodiment of the invention that the drain pan is not arranged directly at the weighing cell, but rather indirectly via at least one holder and, optionally, components of the housing of the weighing cell.

It is conceivable that the damper has at least one feed-through through which the holder extends at least sectionally. This holder can be formed circular in cross-section, but any desired other feed-through is also conceivable and covered by the invention.

The feed-through preferably extends in a perpendicular direction through the damper.

The damper can have a longitudinal axis and the feed-through preferably extends along or in parallel with the longitudinal axis.

The feed-through is preferably located at the center of the damper or extends through its central region.

Provision is made in a further embodiment of the invention that the damping device has at least one force transmission element, preferably at least one base plate, which extends between the damper and the housing of the weighing cell. In this embodiment of the invention, the damper is thus not directly connected to the housing of the weighing cell. At least one force transmission element, e.g. of metal or plastic, is rather arranged between the damper and the housing of the weighing cell and transmits the force acting on the damper to the weighing cell or to its housing.

It can in this respect be a base plate which is arranged between the damper and housing of the weighing cell. It is conceivable that the base plate is arranged between the damper and the installation plate of the housing of the weighing cell forming the base of the housing. Any other element can generally also be considered which is suitable for such a force transmission. The force transmission element therefore does not necessarily have to be of plate shape.

Provision is made in a further embodiment of the invention that the damping device has at least one force introduction element by means of which the force applied to by the drain pan or by the bags located therein is introduced into the damper. This force introduction element can, for example, be in the form of a top plate or of another element which presses onto the top of the damper or which is arranged above the damper. The force introduction element also does not necessarily have to be of plate shape; any other shape of the force introduction element is conceivable and also covered by the invention.

The force introduction element can comprise metal or plastic, for example.

Provision is made in a preferred embodiment of the invention that the force introduction element, such as the top plate, and/or the force transmission element, such as the base plate, has or have a size which corresponds to the surface of the damper which is connected to the force introduction element or to the force transmission element. It is achieved by such a full-area contact that the respectively introduced forces or the forces to be transmitted are transmitted over a relatively large area of the damper and the damping properties are thus ideally utilized.

The damper can be of cylindrical design, but can also have any other desired shape.

The damper preferably comprises rubber or at least consists of rubber. Other damping or elastic materials are also conceivable and are also covered by the connection.

The drain pan can be arranged at at least one holder such as at a linkage or the like which extends sectionally through an opening of the housing in or at which the weighing cell is located, wherein the opening is dimensioned such that the holder does not contact the opening margin of the opening of the housing of the weighing cell in at least one position of the drain pan. It is thereby ensured that a falsification of the measurement result by contact of the holder with a part of the peritoneal dialysis machine is prevented. Provision is preferably made that the named position is the position of the drain pan in which it is located in its non-loaded position of rest.

It is conceivable that the named opening has a diameter which is at least twice as large as the outer diameter of the holder. A certain deflection of the holder, starting from the position of rest, is thus conceivable, with a reliable weight determination by the weighing cell also being possible in the deflected position.

Preferably, the weighing cell is located in or at the machine housing and the drain pan is located beneath the machine housing.

It is preferred for the weighing cell to be located in the machine housing and for the drain pan to be located beneath the machine housing.

To be able to restrict the deformation values of the weighing cell or of the housing of the weighing cell, at least one abutment is preferably provided that limits this deformation.

In a preferred embodiment of the invention, this abutment is located beneath the housing of the weighing cell. The abutment can, for example, be formed as a plate, in particular as a metal plate, that extends beneath the installation plate of the housing of the weighing cell and that is spaced apart therefrom at least region-wise. A steel plate or aluminum plate can be considered, for example.

Such an abutment is therefore preferably provided to restrict the deflection and to be able to reliably intercept the introduction of an inadmissibly high dynamic or static effect of force on the weighing cell.

It is advantageous if this abutment is adjustable. Adjustment means can thus be provided by means of which the spacing between the housing of the weighing cell and the abutment is variable, with provision preferably being made that the adjustment means comprise at least one screw and at least one locknut. It is, for example, conceivable for a screw having a fine thread and an adjustment nut and/or locknut to be used in an adjustable gap between the installation block, i.e. the housing of the weighing cell and the named plate, and for the exact adjustment to be made using the screw.

BRIEF DESCRIPTION OF THE DRAWINGS

Further details and advantages of the invention will be explained in more detail with reference to an embodiment shown in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
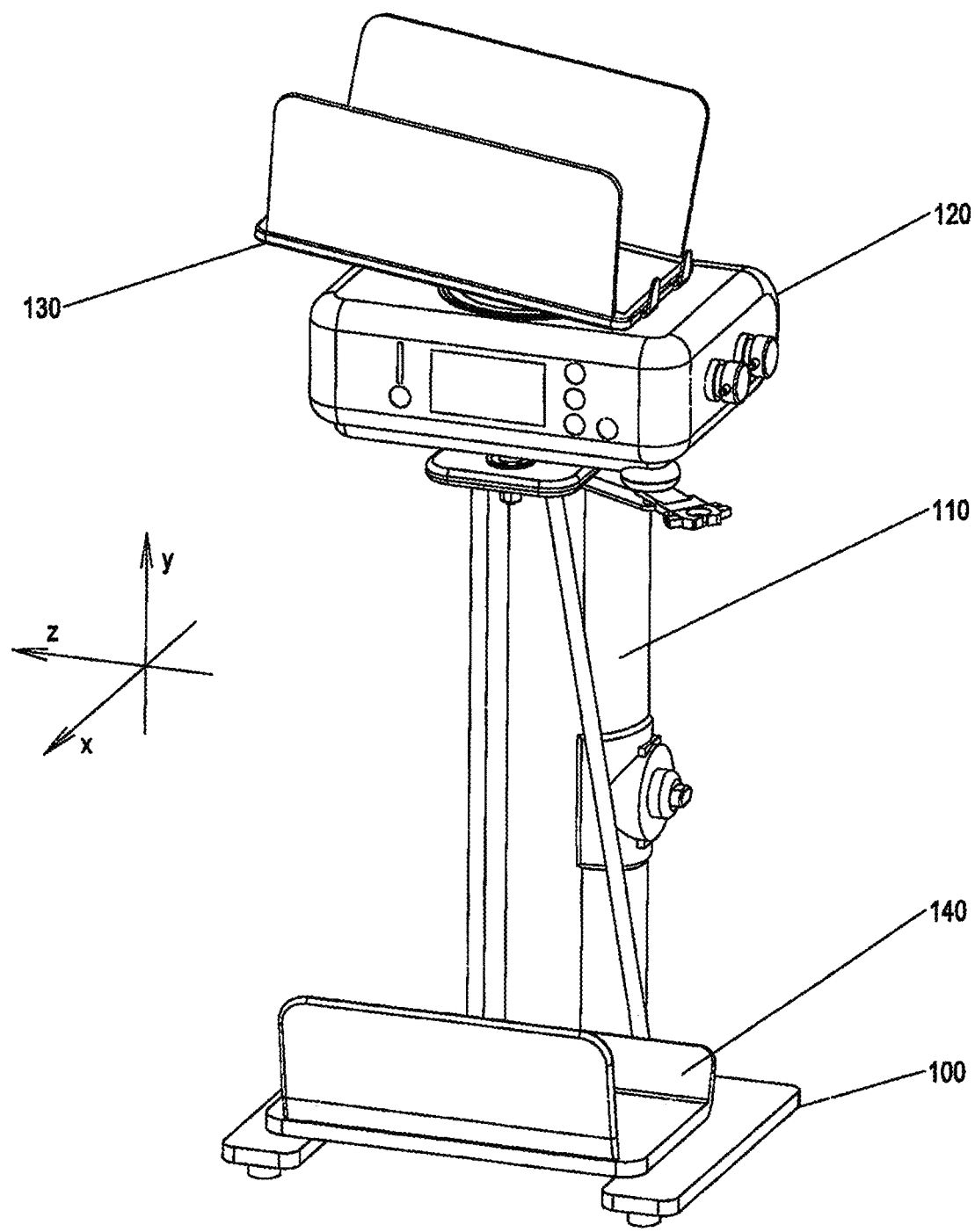
FIG. 1: a perspective view of a peritoneal dialysis machine in accordance with the invention.

A peritoneal dialysis machine in accordance with the invention can be seen from FIG. 1. The machine has a machine stand 100, a housing carrier 110 extending upwardly from this and a machine housing 120 which is arranged at the housing carrier 110.

The control required for the operation of the machine and optionally display and/or operating elements are located in the machine housing 120.

The weighing pan 130 is located above the machine housing 120. Said weighing pan is heatable and serves the receiving of solution bags which contain fresh dialyzate to be supplied to the patient.

Figure 2:
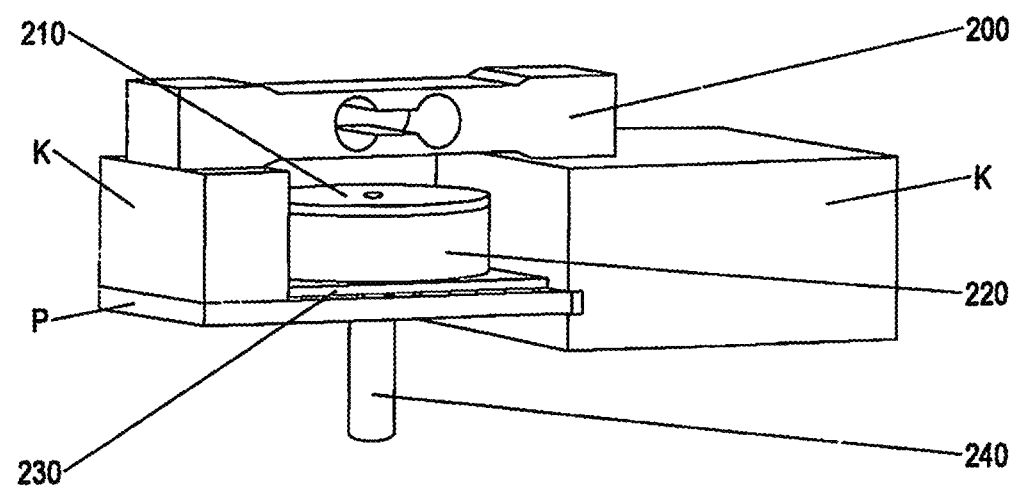
FIG. 2: a perspective sectional view through the damping apparatus with a weighing cell in accordance with the invention.
Figure 3:
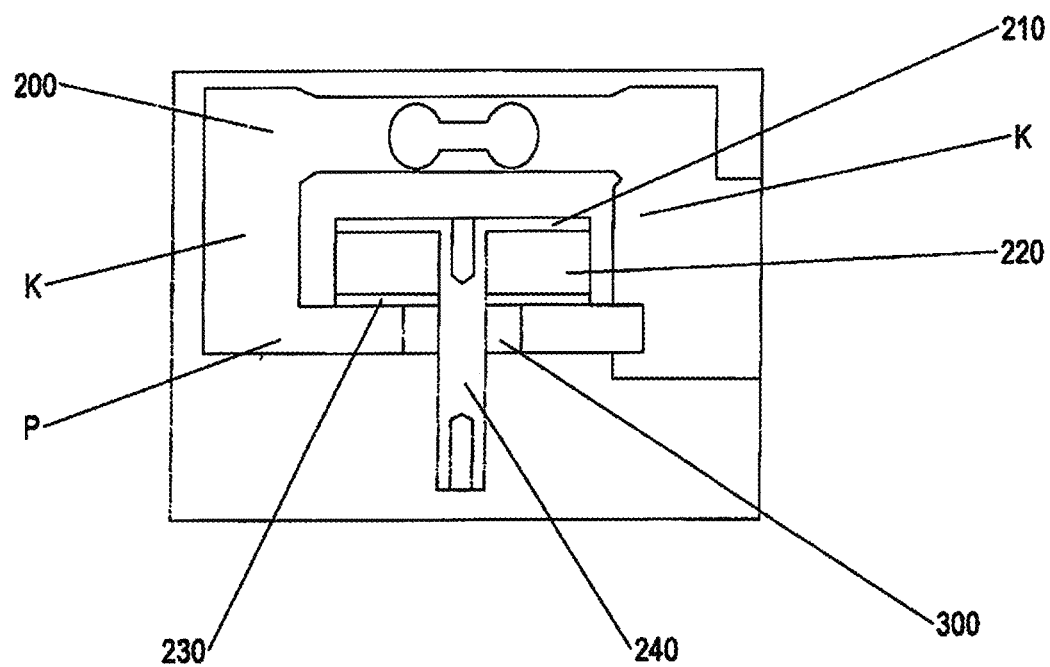
FIG. 3: a schematic sectional view of the arrangement In accordance with FIG. 2.

A weighing cell is arranged in the machine housing 120; it can be seen from FIGS. 2 and 3 and is marked by the reference numeral 200 there.

A holder which is in the form of two rods in accordance with FIG. 1 and at which the drain pan 140 is arranged extends downwardly from this weighing cell or from its housing.

In accordance with the embodiment shown in FIG. 1, the x axis extends, from the viewpoint of a user located in front of the machine, in the depth direction of the drain pan 140; the z axis extends in the width direction of the drain pan 140; and the y axis extends upwardly, that is in parallel with the housing carrier 110.

A load or a torque about the x axis or about the z axis can occur, for example, on an unintended contact of the drain pan 140. A torque about the y axis can occur, for example, if someone rotates the drain pan about this axis.

The damping apparatus in accordance with the present invention serves to damp or reduce the loads on the weighing cell caused by the drain pan.

FIG. 2 shows by reference numeral 200 the weighing cell which is located within the machine housing 120 of the peritoneal dialysis machine.

The weighing cell 200 is arranged in or at a weighing cell housing which comprises an assembly plate P disposed at the bottom and two assembly blocks K extending upwardly starting therefrom. The assembly plate P is located at the bottom, beneath the base plate 230. Two installation blocks K extend upwardly to the right and to the left of the damper 220 from the installation plate P. The installation blocks K are connected at their upper side to the weighing cell 200.

The installation plate P, the two installation blocks K and the weighing cell 200 surround a recess in which the damping apparatus is located.

The damping apparatus comprises a top plate 210, which is e.g. circular, a base plate 230 and the damper 220 which is arranged between the plates 210 and 230. The top plate 210 has the same dimension as the damper 220 so that it terminates flush with the damper. The base plate 230 can likewise have this shape or can also be rectangular or square. The base plate 230 is preferably larger than the damper 220 so that it correspondingly projects at one side or at a plurality of sides.

The force acting on the damper 220 or on the top plate 210 or the acting torque is transmitted to the weighing cell 200 via the base plate 230 and the weighing cell housing.

The reference numeral 240 designates the upper section of a holder or of a linkage to which the drain pan is indirectly or directly fastened.

FIG. 3 again shows the design of the arrangement in accordance with FIG. 2 in a schematic sectional representation.

In this Figure, the same components or components of the same function are marked by the same reference numerals as in FIG. 2.

It can be seen from FIG. 3 that the damper 220 is arranged between the plates 210 and 230.

The housing of the weighing cell 200 or the assembly plate P has a borehole or an opening 300 through which the holder or the rod 240 extends. The base plate 230 also has such a recess. The opening of the base plate 230 can be exactly as large as that of the assembly plate P.

The damper 220 furthermore has a central feed-through which extends vertically and which extends through the longitudinal axis of the damper 220.

The rod 240 extends through this feed-through of the damper 220 and through the borehole 300 or opening of the base plate 230 and of the assembly plate P.

The drain pan 140 is fastened to the rod 240. The weight of the drain pan is thus transmitted via the rod 240 to the plate 210 and from there to the damper 220. The damper 220 transmits the weight via the plate 230 to the housing of the weighing cell 200 and thus to the weighing cell 200. This applies correspondingly to the transmission of torques.

To prevent the holder 240 from abutting the housing of the weighing cell 200, provision is made that the opening 300 of the installation plate P and the opening of the base plate 230 is substantially larger than the outer dimensions of the holder 240. A certain deflection of the holder 240 relative to the position shown in FIG. 3 is thus also conceivable without a falsification of the measurement taking place by a contact with a component of the housing of the weighing cell 200 or of another part. A reliable weight measurement can thus also be carried out in the event of an uneven loading of the drain pan 140.

The damper 220 limits the torque acting on the weighing cell 200 and prevents undue force actions on the weighing cell 200. It furthermore has the object of damping vibrations of the holder 240 or of the drain pan 140.

The damper 220 comprises an elastic material. It preferably comprises rubber, with the invention not being restricted to rubber as the damping material.

The damper 220 is configured such that it applies a counter-torque to the pivot movement of the holder 240 which is so large that the drain pan or the holder does not contact further components of the peritoneal dialysis machine.

FIG. 4 shows the load cell again having the reference numeral 200 and the installation blocks K and the installation plate P that together form the housing of the weighing cell.

Figure 4:
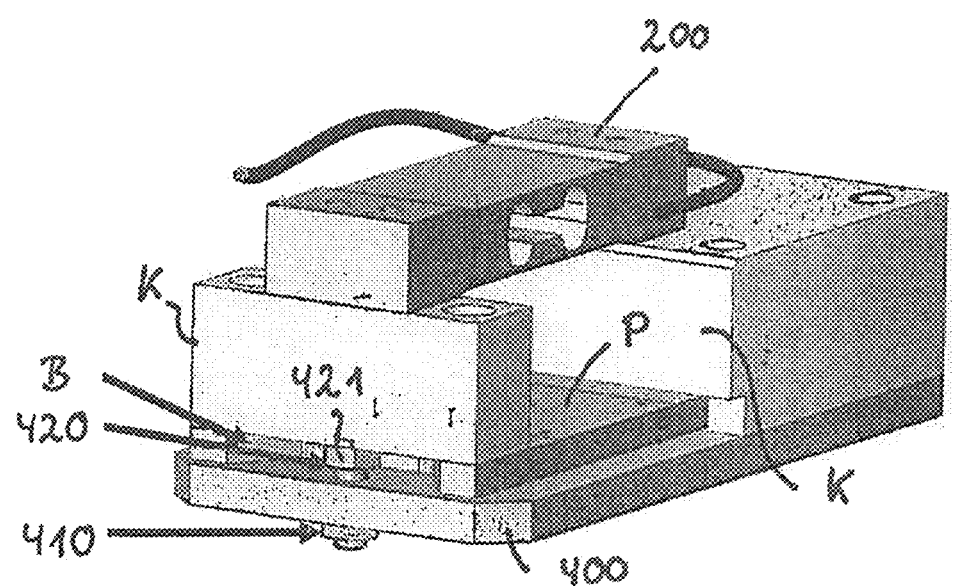
FIG. 4: a schematic view of the housing of the weighing cell with adjustable abutment.

As can furthermore be seen from FIG. 4, a further plate 400 is located beneath the installation plate P and is spaced apart from the installation plate P by a gap.

This plate 400 can, for example, have a thickness of 10 mm in the case of an aluminum plate or 6 mm in the case of a steel plate. The values are purely exemplary here. The thickness of the plate 400 is preferably in a range from 4 mm to 12 mm. The plate is preferably adapted to be able to bear a load of up to 80 kg.

On an overload, the installation plate P impacts the plate 400 or contacts it so that the force is absorbed by the plate 400.

Reference symbol B denotes a cut-out of the installation plate P in which a screw 420 having a fine thread and an adjustment nut 421 are located, with the screw 420 being rotatable through said adjustment nut. The adjustment nut 421 is connected to the screw 420 in a rotationally fixed manner or as one piece. The spacing between the installation plate P and the plate 400, i.e. the abutment, can be exactly changed by rotating the screw 420.

Once the desired spacing has been reached, the screw 420 is fixed, and thus also the size of the gap between the installation plate P and the plate 400, by the locknut 410 that is located beneath the plate 400 and fixes the screw 420 there.

Said setting of the gap dimension can take place before the unit in accordance with FIG. 4 has been inserted into the machine. The adjustment nut 421 is easily reachable due to the lateral arrangement thereof so that the abutment adjustment can be carried out comparatively simply.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A peritoneal dialysis machine comprising:
a machine housing;
a drain pan for receiving one or more solution bags for storing consumed dialyzate, the drain pan being connected to a weighing cell configured to detect a weight of the drain pan;
a damping system configured to prevent an introduction of undue force into the weighing cell, the damping system including a damper to which the drain pan is directly or indirectly fastened, and a force introduction element located above the damper and to which the drain pan is directly or indirectly fastened, with the damper being connected to the weighing cell such that the weight of the drain pan acting thereon is transmitted to the weighing cell; and a holder, which carries the drain pan, and which is arranged directly or indirectly at the damper, with the damper having at least one feed-through through which the holder extends at least sectionally.

2. The peritoneal dialysis machine in accordance with claim 1, wherein the damper has a longitudinal axis, and the feed-through extends along the longitudinal axis or along an axis extending in parallel therewith.

3. The peritoneal dialysis machine in accordance with claim 1, wherein the damping device includes a force transmission element arranged between the damper and a housing of the weighing cell.

4. The A peritoneal dialysis machine in accordance with claim 3, wherein at least one of the force introduction element and the force transmission element has a size which corresponds to a surface of the damper which is connected to at least one of the force introduction element and the force transmission element.

5. The peritoneal dialysis machine according to claim 4, wherein the force introduction element is a base plate, and the force transmission element is a top plate.

6. The peritoneal dialysis machine according to claim 3, wherein the force transmission element is a base plate.

7. The peritoneal dialysis machine in accordance with claim 1, wherein the weighing cell is arranged in or at the machine housing.

8. The peritoneal dialysis machine in accordance with claim 1, wherein the damper is cylindrical.

9. The peritoneal dialysis machine in accordance with claim 1, wherein the damper includes rubber, or consists of rubber.

10. The peritoneal dialysis machine in accordance with claim 1, wherein the holder extends through an opening of the housing of the weighing cell, with the opening being dimensioned such that the holder does not contact a space of the opening in at least one position of the drain pan.

11. The peritoneal dialysis machine in accordance with claim 10, wherein the at least one position is that in which the drain pan is located in a non-loaded position of rest.

12. The peritoneal dialysis machine according to claim 11, wherein the opening of the housing of the weighing cell has a diameter which is at least twice as large as an outer diameter of the holder.

13. The peritoneal dialysis machine in accordance with claim 1, wherein the drain pan is located beneath the machine housing and the weighing cell is located in the machine housing.

14. The peritoneal dialysis machine in accordance with claim 1, wherein an abutment is located beneath the housing of the weighing cell to limit deflection of the housing of the weighing cell.

15. The peritoneal dialysis machine in accordance with claim 14, wherein the abutment is configured as a plate that extends beneath an installation plate and is spaced apart therefrom at least region-wise.

16. The peritoneal dialysis machine according to claim 15, wherein the abutment configured as a plate has a material of construction that is a metal.

17. The peritoneal dialysis machine in accordance with claim 14, further comprising an adjustment means for varying a spacing between the housing of the weighing cell and the abutment.

18. The peritoneal dialysis machine according to claim 17, wherein the adjustment means includes a screw and a locknut.

19. The peritoneal dialysis machine according to claim 14, wherein the abutment is adjustable.

20. The peritoneal dialysis machine according to claim 1, wherein the force introduction element is a top plate.

21. The peritoneal dialysis machine according to claim 1, wherein the feed-through has a circular cross-section.

* * * * *